US011298415B2

(12) United States Patent
Koley et al.

(10) Patent No.: US 11,298,415 B2
(45) Date of Patent: Apr. 12, 2022

(54) **ALGINATE CHITOSAN NANOFORMULATION OF OMPA—A *SHIGELLA* PROTEIN SUBUNIT**

(71) Applicant: Indian Council of Medical Research, New Delhi (IN)

(72) Inventors: Hemanta Koley, Kolkata (IN); Priyadarshini Mukherjee, Kolkata (IN); Dhrubajyoti Nag, Kolkata (IN); Ritam Sinha, Kolkata (IN); Manoj Kumar Chakrabarti, Kolkata (IN)

(73) Assignee: Indian Council of Medical Research, New Delhi (IN)

( * ) Notice: Subject to any disclaimer, the term of this patent is extended or adjusted under 35 U.S.C. 154(b) by 0 days.

(21) Appl. No.: 16/093,237

(22) PCT Filed: Apr. 28, 2017

(86) PCT No.: PCT/IN2017/000094
§ 371 (c)(1),
(2) Date: Oct. 12, 2018

(87) PCT Pub. No.: WO2017/191646
PCT Pub. Date: Nov. 9, 2017

(65) Prior Publication Data
US 2019/0060436 A1 Feb. 28, 2019

(30) Foreign Application Priority Data
May 2, 2016 (IN) ............................ 201611015219

(51) Int. Cl.
*A61K 39/112* (2006.01)
*A61K 9/51* (2006.01)
*A61P 31/04* (2006.01)
*A61K 47/36* (2006.01)
*A61K 39/00* (2006.01)

(52) U.S. Cl.
CPC ........ *A61K 39/0283* (2013.01); *A61K 9/5161* (2013.01); *A61K 47/36* (2013.01); *A61P 31/04* (2018.01); *A61K 2039/542* (2013.01); *A61K 2039/55555* (2013.01); *Y02A 50/30* (2018.01)

(58) Field of Classification Search
CPC ... A61P 31/04; Y02A 50/476; A61K 39/0283; A61K 9/5161; A61K 2039/542; A61K 47/36; A61K 2039/55555
See application file for complete search history.

(56) References Cited

PUBLICATIONS

Gao et al., (Vaccine. vol. 31. Issue 48, Nov. 19, 2013, pp. 5754-5759). (Year: 2013).*
Zheng et al., (Biochemical and Biophysical Res Comms vol. 323, Issue 4; Oct. 2004: pp. 1321-1327). (Year: 2004).*
Nanda et al., (Biologicals. vol 42, Issue 3. May 2014; pp. 153-159) (Year: 2014).*
Li et al., (Preparation of alginate coated chitosan microparticles for vaccine delivery. BMC Biotechnol 8, 89 (2008). https://doi.org/10.1186/1472-6750-8-89). (Year: 2008).*
(Continued)

*Primary Examiner* — Jana A Hines
(74) *Attorney, Agent, or Firm* — The Webb Law Firm

(57) ABSTRACT

Provided herein is a Formulation of OmpA including a) OmpA protein as active molecule obtained as a product of OmpA gene inserted in a plasmid comprising a novel set of forward and reverse primer set, and b) Alginate chitosan nanoparticles as vehicle.

7 Claims, 5 Drawing Sheets

Specification includes a Sequence Listing.

(56) References Cited

PUBLICATIONS

Pore et al., (PLOS One. Jul. 2011. vol. 6, Issue7. e22663, p. 1-11) (Year: 2011).*
Dubey et al., (Vaccines. 2016, 4, 40) (Year: 2016).*
Arriola et al., (J. Sci Food Agric 2013; 93: 1525-1536) (Year: 2013).*
Biswas et al, "Development and characterization of alginate coated low molecular weight chitosan nanoparticles as new carriers for oral vaccine delivery in mice", Carbohydrate Polymers, 2015, pp. 403-410, vol. 121.
Borges et al, "Evaluation of the immune response following a short oral vaccination schedule with hepatitis B antigen encapsulated into alginate-coated chitosan nanoparticles", European Journal of Pharmaceutical Sciences, 2007, pp. 278-290, vol. 32.
Katas et al, "Development of Chitosan Nanoparticles as a Stable Drug Delivery System for Protein/siRNA", International Journal of Biomaterials, 2013, pp. 1-9, vol. 2013.
Kumar Kosta et al, "Chitosan Nanoparticle—A Drug Delivery System", International Journal of Pharmaceutical & Biological Archives, 2012, pp. 737-743, vol. 3(4).
Nagpal et al, "Chitosan Nanoparticles: A Promising System in Novel Drug Delivery", Chem. Pharm. Bull., 2010, pp. 1423-1430, vol. 58(11).
Oliveira et al, "A New Strategy Based on Smrho Protein Loaded Chitosan Nanoparticles as a Candidate Oral Vaccine against Schistosomiasis", Plos Neglected Tropical Diseases, 2012, pp. 1-13, vol. 6(11).
Pore et al, "Outer Membrane Protein A (OmpA) of Shigella flexneri 2a, Induces Protective Immune Response in a Mouse Model", PLOS ONE, 2011, pp. 1-11, vol. 6(7).
Pore et al, "Outer membrane protein A (OmpA) from Shigella flexneri 2a: A promising subunit vaccine candidate", VACCINE, 2013, pp. 3644-3650, vol. 31(36).
Sailaja et al., "Chitosan nanoparticles as a drug delivery system", Research Journal of Pharmaceutical, Biological and Chemical Sciences, 2010, pp. 474-484, vol. 1, Issue 3.

* cited by examiner

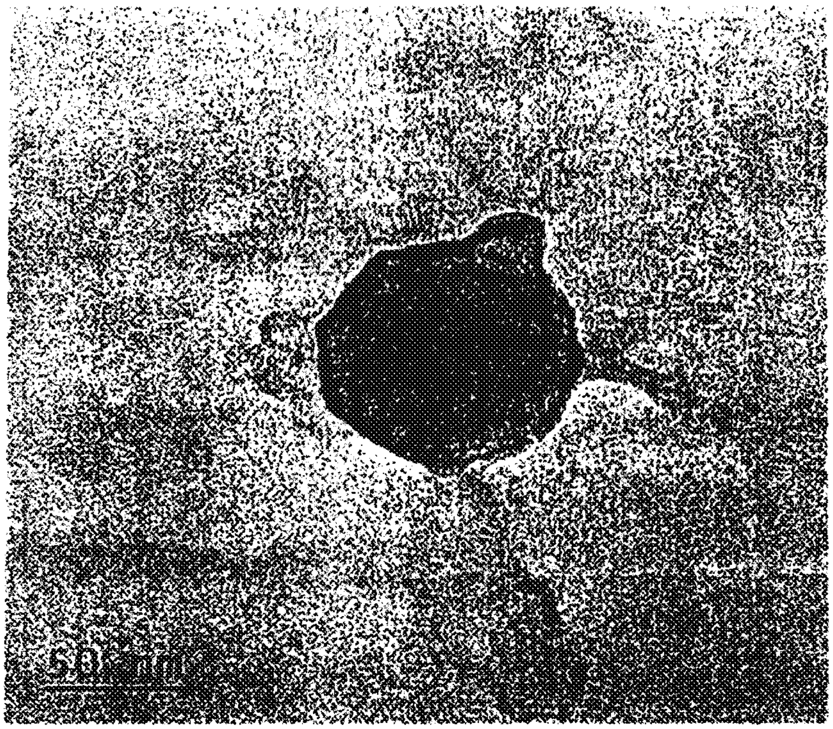
Figure : 1
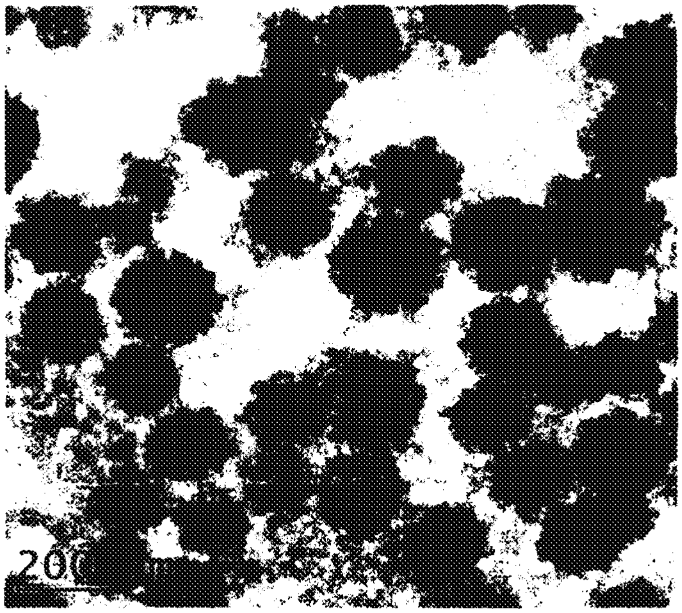
Figure : 2

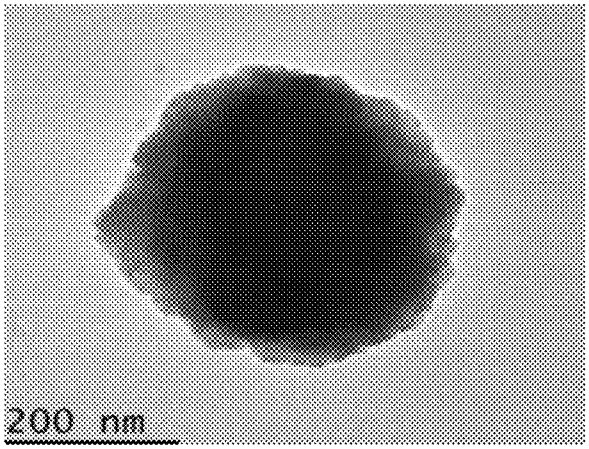
Figure : 2a
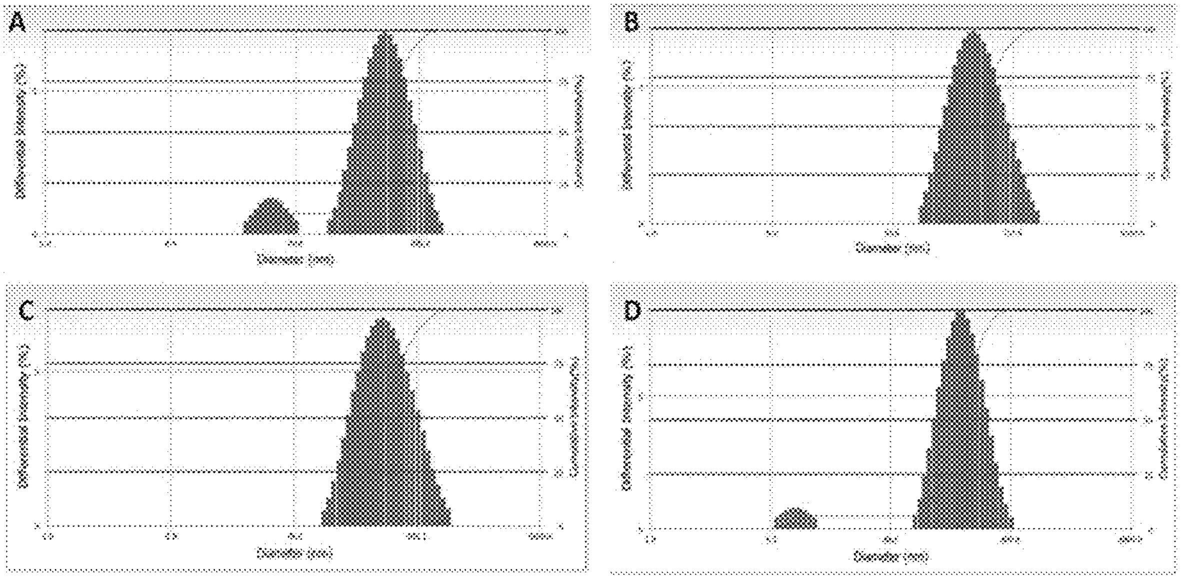
Figure : 3

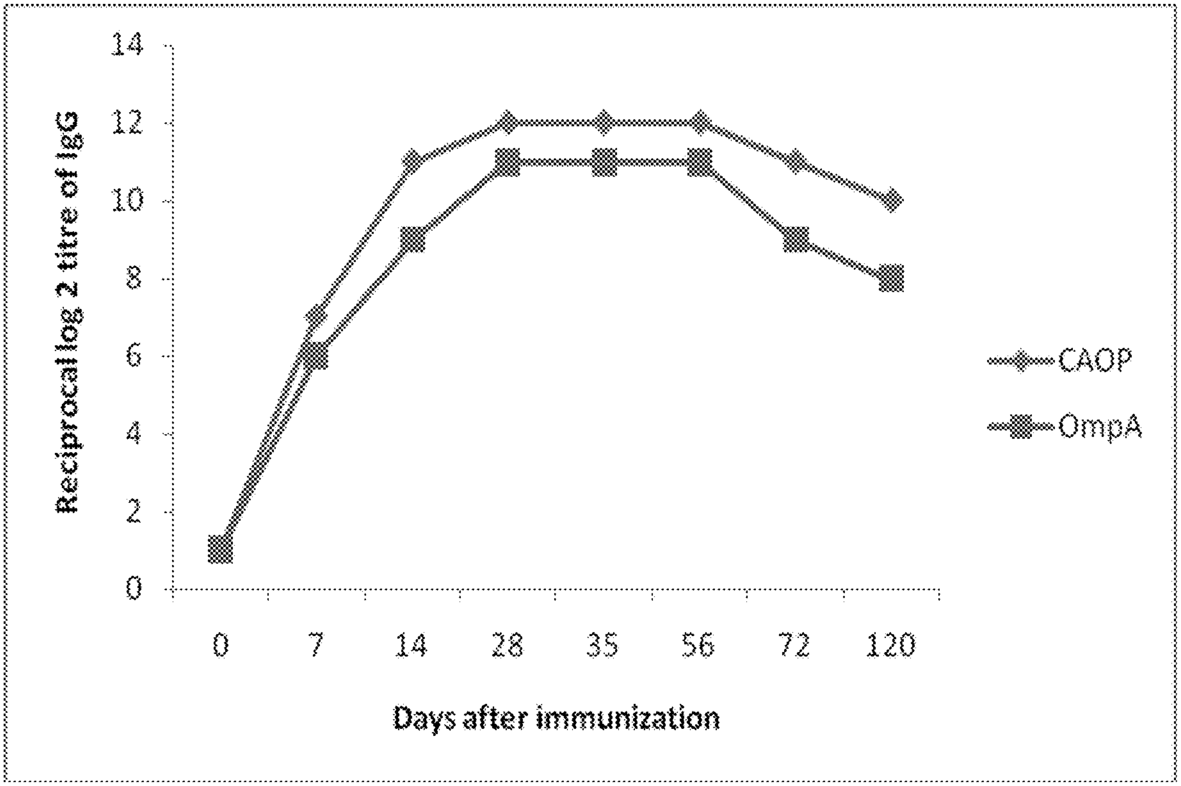
Figure : 4
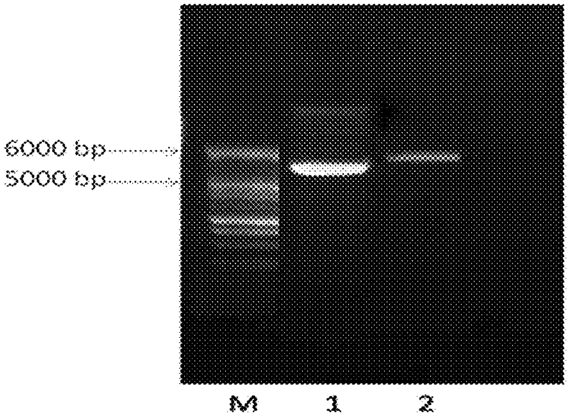
Figure : 5

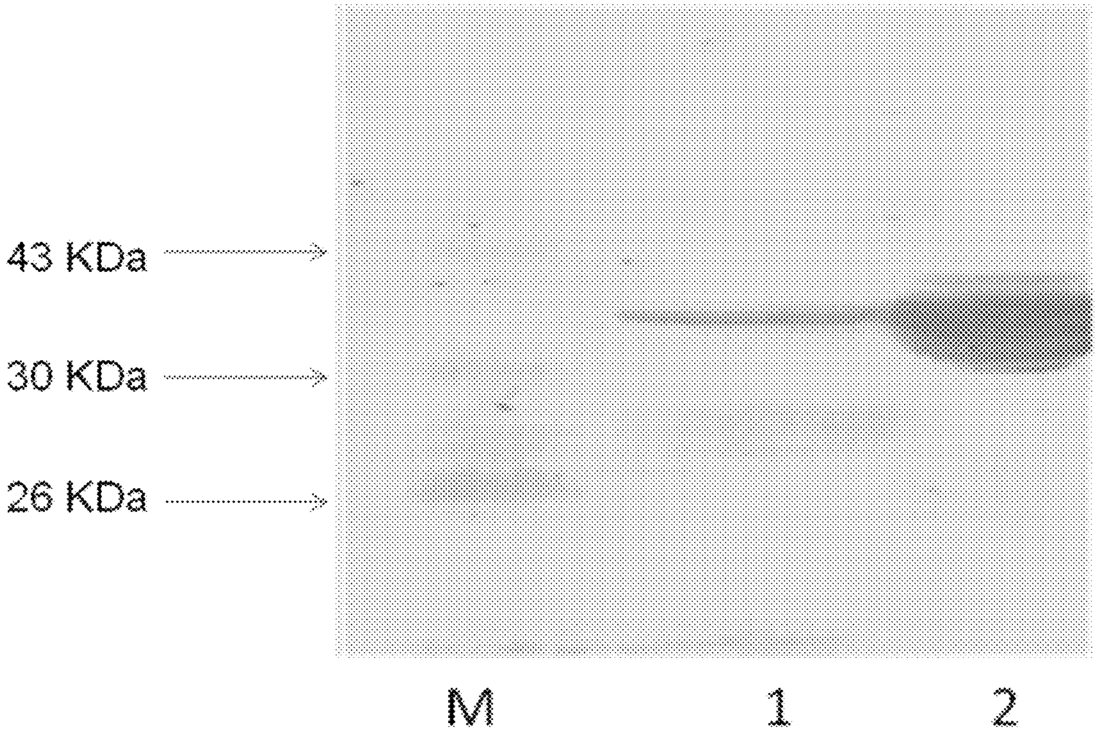
Figure : 6
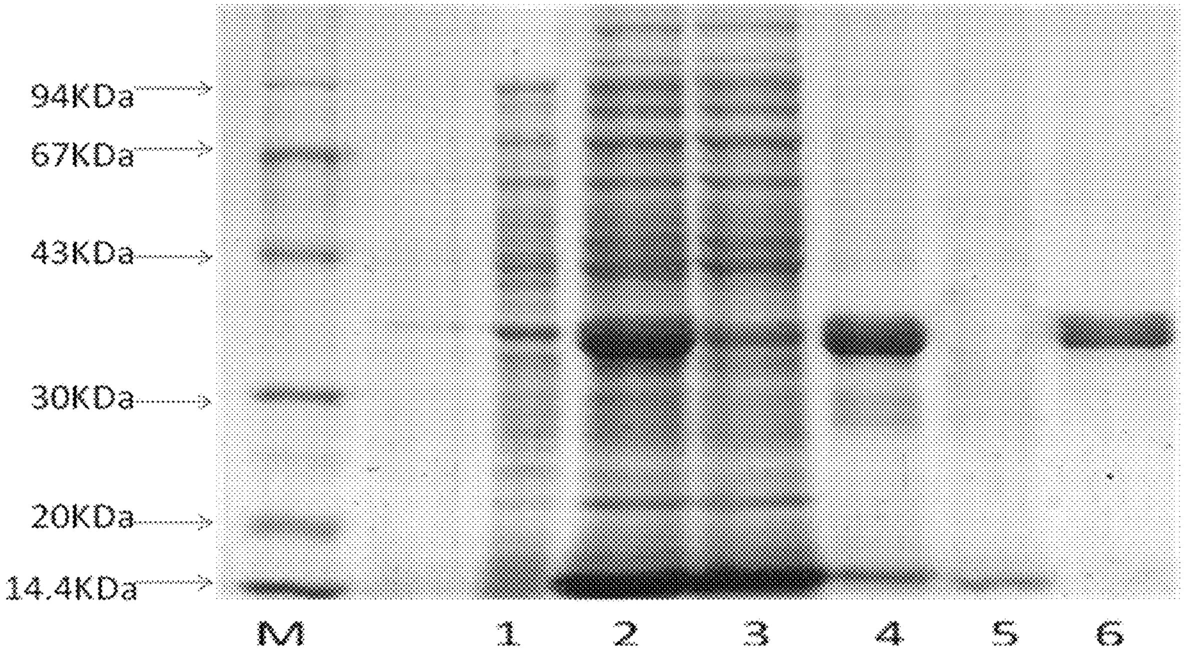
Figure : 7

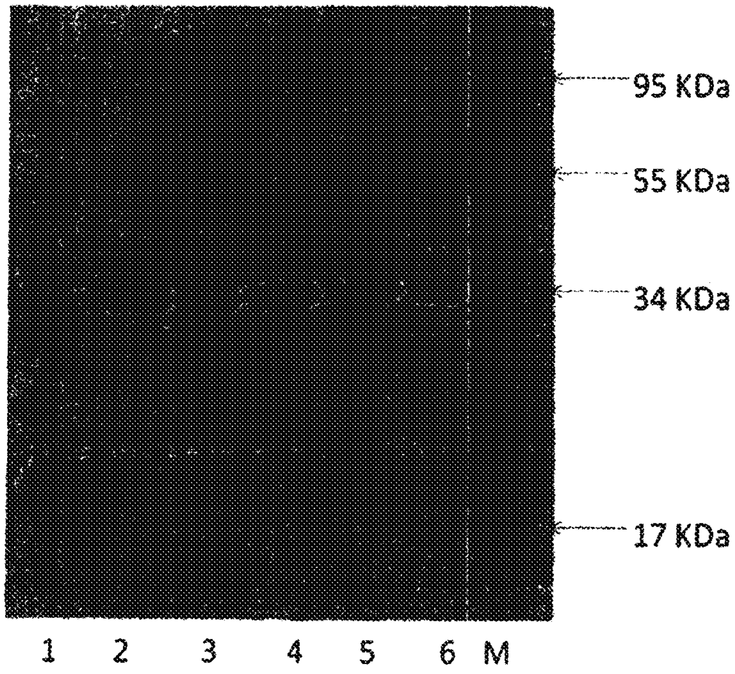
Figure : 8

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: OmpA Forward Primer

<400> SEQUENCE: 1

aaaaagacac atatgcgatt gcag                                        24


<210> SEQ ID NO 2
<211> LENGTH: 27
<212> TYPE: DNA
<213> ORGANISM: Artificial Sequence
<220> FEATURE:
<223> OTHER INFORMATION: OmpA Reverse Primer

<400> SEQUENCE: 2

gtatctcgag agcttgcgct gagttac                                     27


<210> SEQ ID NO 3
<211> LENGTH: 27
<212> TYPE: DNA
<213> ORGANISM: Artificial Sequence
<220> FEATURE:
<223> OTHER INFORMATION: OmpA Internal Primer

<400> SEQUENCE: 3

accaggttaa cccgtatgtt ggctttg                                     27


<210> SEQ ID NO 4
<211> LENGTH: 28
<212> TYPE: DNA
<213> ORGANISM: Artificial Sequence
<220> FEATURE:
<223> OTHER INFORMATION: OmpA Internal Primer

<400> SEQUENCE: 4

tgttgagtac gcgatcactc ctgaaatc                                    28


<210> SEQ ID NO 5
<211> LENGTH: 29
<212> TYPE: DNA
<213> ORGANISM: Artificial Sequence
<220> FEATURE:
<223> OTHER INFORMATION: OmpA Internal Primer
```

-continued

<400> SEQUENCE: 5
gttcaacttc aacaaagcaa ccctgaaac 29

<210> SEQ ID NO 6
<211> LENGTH: 22
<212> TYPE: DNA
<213> ORGANISM: Artificial Sequence
<220> FEATURE:
<223> OTHER INFORMATION: OmpA Internal Primer

<400> SEQUENCE: 6
tcggacagac cctggttgta ag 22

<210> SEQ ID NO 7
<211> LENGTH: 24
<212> TYPE: DNA
<213> ORGANISM: Artificial Sequence
<220> FEATURE:
<223> OTHER INFORMATION: OmpA Internal Primer

<400> SEQUENCE: 7
agctggagcc ggagcaacta ctgg 24

<210> SEQ ID NO 8
<211> LENGTH: 26
<212> TYPE: DNA
<213> ORGANISM: Artificial Sequence
<220> FEATURE:
<223> OTHER INFORMATION: OmpA Internal Primer

<400> SEQUENCE: 8
ctgagctttg tatgcaccgt tttcaa 26

<210> SEQ ID NO 9
<211> LENGTH: 1047
<212> TYPE: DNA
<213> ORGANISM: Shigella flexneri

<400> SEQUENCE: 9
atgaaaaaga cagctatcgc gattgcagtg gcactggctg gtttcgctac cgtagcgcag 60
gccgctccga aagataacac ctggtacact ggtgctaaac tgggctggtc ccagtaccat 120
gacactggtt ttattcctaa caatggtccg acccacgaaa accaactggg tgcaggtgct 180
tttggtggtt accaggttaa cccgtatgtt ggttttgaaa tgggttacga ctggttaggt 240
cgtatgccgt acaaaggcga caacatcaac ggcgcataca aagctcaggg cgttcagctg 300
accgctaaac tgggttaccc aatcactgac gatctggaca tctacactcg tctgggtggt 360
atggtatggc gtgcagacac caaggctaac gtacctggtg gcgcatcctt taaagaccac 420
gacactggcg tttctccggt tttcgcaggt ggtgttgagt acgcgatcac tcctgaaatc 480
gctacccgtc tggaatacca gtggaccaac aacatcggtg acgcaaacac catcggtact 540
cgtccggaca acggtctgct gagcctgggt gtttcctacc gtttcggtca gggcgaagca 600
gctccggtag ttgctccagc tccggcaccg gaagtacaga ccaagcactt cactctgaag 660
tctgacgttc tgttcaactt caacaaagca accctgaaac cggaaggtca ggctgctctg 720
gatcagctgt acagccagct gagcaaccta gatccgaaag acggttccgt agttgttctg 780
ggttacactg accgcatcgg ttctgacgct tacaaccagg gtctgtccga gcgccgtgct 840
cagtctgttg ttgattacct gatctccaaa ggtatcccgg cagacaagat ctccgcacgt 900

-continued

```
ggtatgggcg aatccaaccc ggttactggc aacacctgtg acaacgtgaa acagcgtgct    960

gcactgatcg actgcttggc tccggatcgt cgcgtagaga tcgaagttaa aggtatcaaa   1020

gacgttgtaa ctcagccgca ggcttaa                                       1047
```

ALGINATE CHITOSAN NANOFORMULATION OF OMPA—A *SHIGELLA* PROTEIN SUBUNIT

This application is the United States national phase of International Application No. PCT/IN2017/000094 filed Apr. 28, 2017, and claims priority to Indian Patent Application No. 201611015219 filed May 2, 2016, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1803279_ST25.txt. The size of the text file is 3,346 bytes, and the text file was created on Apr. 17, 2018.

FIELD OF THE INVENTION

This invention relates to a formulation for immunogen improved delivery system and a process for the preparation thereof.

This invention further relates to a novel immunogen delivery system comprising an alginate chitosan nanoformulation of OmpA, a *Shigella* protein subunit vaccine against shigellosis.

BACKGROUND OF THE INVENTION

Shigellosis is one of the major diarrheal diseases leading to high morbidity levels among the elderly and infant populations. But there is no potent vaccine available to prevent. Scientists and academician are trying to prepare a vaccine against shigellosis.

Endogenous peptides, protein, and oligonucleotides are among the main drugs which attract much attention because of their great potentials in treating chronic diseases. However, the extreme in vivo environment of human body has always limited the therapeutic applications of these substances. Polymeric nanoparticles have attracted much attention as delivery systems due to their ability in overcoming the physiological barriers and protecting and targeting the loaded substances to specific cells. Naturally occurring polymers such as chitosan (CS) have been studied to form nanoparticles. CS is a biodegradable polysaccharide, and it is derived from deacetylation of chitin. Apart from its biocompatibility, the low toxicity, hemostatic, and bacteriostatic properties also contribute to its various applications in pharmaceutical field. Several anions have been investigated to crosslink CS like sodium sulphate and dextran sulphate (DS). DS is able to modify protein and siRNA entrapment efficiency (EE) without the use of hardening agents and control the rate of drug release due to its high charge density. Besides DS is a cheap material, it produces mechanically more stable nanoparticles compared to the pentasodium tripolyphosphate (TPP).

Chitosan nanoparticles have been used in the art as a novel drug delivery system. The chitosan nanoparticles, because of their biodegradability, biocompatibility, better stability, low toxicity, simple and mild preparation methods, offer a valuable tool to novel drug delivery systems in the present scenario. Besides ionotropic gelation method, other methods such as microemulsion method, emulsification solvent diffusion method, polyelectrolyte complex method, emulsification cross-linking method, complex coacervation method and solvent evaporation method are also in use. The chitosan nanoparticles have also been reported to have key applications in parentral drug delivery, per-oral administration of drugs, in non-viral gene delivery, in vaccine delivery, in ocular drug delivery, in electrodeposition, in brain targeting drug delivery, in stability improvement, in mucosal drug delivery in controlled drug delivery of drugs, in tissue engineering and in the effective delivery of insulin. The publication 'Chitosan nanoparticles: a promising system in novel drug delivery', to Nagpal K[1]. Singh S K, Mishra D N., and Chem Pharm Bull (Tokyo). 2010 November; 58(11): 1423-30, discloses the origin and properties of chitosan and its nanoparticles along with the different methods of its preparation and the various areas of novel drug delivery where it has got its application.

The article Chitosan nanoparticles as a drug delivery system to A Krishna Sailaja, P. Amareshwar and P. Chakrabarty (Research Journal of Pharmaceutical, Biological and Chemical Sciences) is a review article which summarises the available preparation techniques and the various applications of Chitosan. The article 'Development of Chitosan nanoparticles as a stable drug delivery system for protein/siRNA, to Haliza Katas et al (International Journal of Bio-materials, vol. 2013 (2013) Article ID146320', discloses the modulation of preparative parameters on the physical characteristics and colloidal stability of CS NPs. CS NPs were fabricated by ionic interaction with dextran sulphate (DS) prior to determination of their storage stability. The smallest CS NPs of nm with a surface charge of mV were produced when CS and DS were mixed at pH 4 and with a DS:CS mass ratio of 0.5:1. An entrapment efficiency of 98% was achieved when BSA/siRNA was loaded into the nanoparticles.

The article 'Chitosan Nanoparticle—A Drug Delivery System', to Ashish Kumar Kosta, T. MohitSolakhia, Dr. Shikha Agrawal International Journal of Pharmaceutical 86 Biological Archives 2012; 3(4):737-743 discloses that Chitosan Nanoparticles are good drug carriers because of their good biocompatibility and biodegradability, and can be readily modified. As a new drug delivery system, they have attracted increasing attention for their wide applications. This paper reviews was published on Chitosan Nanoparticles including its preparation methods, modification, and applications.

However, nothing in the prior art discloses a formulation for delivery of immunogen OmpA, which can protect the protein from the acid barrier in the stomach and increase the bioavailability of the protein.

Hence, there is a need in the art to provide a formulation for delivery of the immunogen, which gives higher immunogenicity and protective efficacy than OmpA protein used alone.

OBJECTS OF THE INVENTION

It is therefore the principal object of the present invention is to design a vaccine comprising OmpA nanoformulations as active molecule vehicle upon chitosan nanoparticles.

Another object of the invention is to provide a formulation for immunogen delivery system helping to protect the immunogen from the acid barrier of the stomach.

Yet another object of the invention is to provide a formulation for immunogen delivery system, which increases the bioavailability, biodegradability, biocompatibility of the immunogen.

Still another object of the invention is to provide a formulation for immunogen delivery system, which gives higher immunogenicity and protective efficacy over OmpA protein used alone with better stability and low toxicity.

Further another object of the present invention is to design novel primer according to the sequences of ompA gene.

Still further object of the present invention is to design a readily reproducible plasmid comprising ompA gene along with the novel primers.

SUMMARY OF THE INVENTION

A novel formulation for improved immunogen delivery system comprises substantially effective amount of alginate chitosan nanoparticles with OmpA protein of *Shigella* species. Alginate chitosan nano formulations of OmpA comprises essentially of OmpA protein as active molecule obtained as a product of ompA gene inserted in a plasmid comprising a novel set of forward and reverse primer set having novel sequences of

```
5'-AAAAAGACACATATG CG ATT GCAG-3'

5'-GTATCTCGAGAGCTTGCGCTGAGTTAC-3'
```

and alginate chitosan nanoparticles as vehicle.

A method of preparation of alginate chitosan nano formulation, said method comprising the steps of designing a plasmid comprising novel ompA forward and reverse primer set as insert wherein the underlined bases in the forward primer represents restriction site specific for NcoI and the underlined bases in the reverse primer represents restriction site specific for XhoI; transferring said recombinant plasmid to *E. coli* BL21 (DE3) for multiplication; isolation of OmpA protein as a product from the *E. coli* BL21 (DE3) in the mid log phase of said bacteria wherein the transposable genetic material comprising essentially of said recombinant plasmid insert containing ompA forward and reverse primer set as insert forward and reverse primer set as insert; preparation of chitosan nanoparticles; and loading of OmpA protein to said chitosan nanoparticles.

The preparation of chitosan nanoparticles comprising the steps of preparation of chitosan solution by dissolving chitosan in 1% (v/v) acetic acid solution at concentration of 2 mg/ml; preparation of anionic tripolyphosphate (TPP) solution by dissolving TPP in distilled water at the concentration of 1 mg/ml; addition of TPP solution into chitosan solution dropwise at 1:2 ratio; formation of chitosan colloid nanoparticles under mild agitation in room temperature condition; formulation of colloid chitosan nanoparticles at room temperature which was centrifuged at 35,000 rpm for 1 hr.; discarding of supernatant and re-dispersing of the deposit in distilled water; and final collection of the alginate coated chitosan nanoparticles.

The method of loading of OmpA protein to said chitosan nanoparticles comprises the steps of re-dispersion of colloid said chitosan nanoparticles in 25 ml of distilled water at concentration of 2 mg/mL under continuous ultrasonication to disaggregate the nanoparticles; incubating OmpA protein obtained as a product from the *E. coli* BL21 (DE3) with said nanoparticles under mild agitation at room temperature condition for 15 minutes to make final concentration of OmpA protein 1 mg/mL; loading of OmpA protein subunit to the chitosan nanoparticles by incubating OmpA with said nanoparticles under mild agitation for 15 minutes in room temperature condition; dropwise addition of OmpA loaded chitosan nanoparticles with pH 5.1 to the sodium alginate solution under mild agitation at pH 7 for 10-20 minutes; and final collection of the alginate coated chitosan nanoparticles into calcium chloride ($CaCl2$) aqueous solution at concentration of 0.524 mmol/L to crosslink the alginate layer, presents on the surface of the nanoparticles.

BRIEF DESCRIPTION OF THE ACCOMPANYING DRAWINGS

FIG. 1 Illustrates TEM image of chitosan Nano particle.

FIGS. 2A-2B illustrate TEM image of OmpA coated with chitosan and alginate.

FIG. 3 Illustrates intensity distribution of A) Chitosan, B) Chitosan with alginate, C) OmpA loaded chitosan with alginate (CAOP), D) Alginate.

FIG. 4 Illustrates Serum immunoglobulin titers in immunized sera were measured against OmpA protein of *Shigella* sp.

FIG. 5 Illustrates agarose gel electrophoresis M-Marker, 1-pET28a plasmid, 2-pET28a plasmid with OmpA gene.

FIG. 6 Illustrates western blotting with anti his-tagged antibody. M-Protein pre-stained molecular weight marker, 1-BL21 *E. coli* containing OmpA without IPTG, 2-BL21 *E. coli* containing OmpA induced by IPTG FIG. 7 Illustrates SDS-PAGE of OmpA. M-Marker, 1-Whole cell lysate of BL21 *E. coli* containing OmpA without IPTG, 2-Whole cell lysate of BL21 *E. coli* containing OmpA induced by IPTG, 3-In Supernatant, 4-In pellet as inclusion body, 5-In Wash buffer no protein, 6-purified fraction of OmpA in Elution buffer FIG. 8 Illustrates western blot analysis of recombinant OmpA of *S. flexneri* 2a with antisera from CAOP immunized mice with the whole-cell lysate of *Shigella* lane 1. *S. dysenteriae* 1Δstx NT4907, lane 2. *S. boydii* type 4 BCH612, lane 3. *S. sonnei* IDH00968, lane 4. *S. flexneri* 2a 2457T, lane 5. *S. flexneri* 3a C519, and lane 6. *S. flexneri* 6 C347.

DETAILED DESCRIPTION OF THE PREFERRED EMBODIMENTS

This according to the invention is provided a formulation for immunogen delivery system and a process for the preparation thereof.

In accordance with this invention, a novel formulation for immunogen delivery method has been developed by using chitosan alginate nano formulation with OmpA protein (CAOP) of *Shigella* sp. and the protective efficacy and immunogenicity of CAOP against homologous as well as heterologous *Shigella* strains in animal model has been studied. Also the duration of protection offered by CAOP has been studied.

Sodium-alginate and chitosan both are extensively used in encapsulation of drug for the purpose of sustained release. These are polysaccharide polymers, formed of repeating units joined together by glycosidic bond. Both polymers have the properties of an ideal carrier for drug delivery, such as biocompatibility, biodegradability, non-toxicity, and low cost. Thus the formulation prepared from chitosan alginate nanoparticle will effectively deliver the OmpA in the gut epithelia. The controlled release of OmpA from the said nanoformulations could maintain steadier levels of this protein in bloodstream for longer durations.

Chitosan nanoparticles are prepared by the ionic gelation of Chitosan Solution with anionic tripolyphosphate (TPP). Briefly, chitosan was dissolved in 1% (v/v) acetic acid aqueous solution at concentration of 2 mg/ml. Then, TPP was dissolved in distilled water at the concentration of 1 mg/ml. Subsequently, TPP solution was added drop wise into chitosan solution at 1:2 ratio. Chitosan colloid nanoparticles formed spontaneously under mild agitation at room temperature. Two hours later, chitosan colloid nano particles was centrifuged at 35,000 rpm for 1 hr. Then, the supernatant was discarded and the deposit was re-dispersed in distilled water.

After the preparation of chitosan nanoparticle, it is loaded with OmpA.

The loading of OmpA procedure has been given below:

Colloid chitosan nanoparticles were then re-dispersed in 25 ml of distilled water at concentration of 2 mg/ml under continuous ultrasonication to disaggregate the chitosan nano particles. The loading procedure was performed by incubating OmpA with chitosan nano particles under mild agitation at room temperature for 15 min so that final concentration of OmpA protein 1 mg/ml.

Preparation of alginate coated chitosan nano particles:

OmpA loaded chitosan nanoparticles suspensions with pH value at 5.1 were added drop wisely into sodium alginate solution (pH=7.2) at concentration of 1 mg/ml under mild agitation for 10 min. Then the suspension was centrifuged at 3,400 rpm for 5 min, and the supernatant was discarded.

Finally, alginate coated chitosan nano particles were re-dispersed into calcium chloride ($CaCl_2$) aqueous solution (pH=7.0) at concentration of 0.524 mmol/L to crosslink the alginate layer presents on the surface of chitosan nano particles.

The final formulation of OmpA loaded chitosan alginate is clearly disclosed in accordance with FIG. 2.

FIG. 3 illustrates the intensity distribution of a) chitosan, b) chitosan with alginate, c) OmpA loaded chitosan with alginate (CAOP) d) Alginate.

The cloning of OmpA protein has been given below:

a) Sequence of OmpA gene:

The ompA gene was searched out from NCBI genome sequence of *Shigella flexneri* 2a 2457T. This sequence was used for designing of primers required for cloning.

The sequence was used for designing of primers required for cloning. The primers are designed from the upstream and downstream sequence of ompA gene using commercially available primer designing software. Two novel restriction sites were introduced in the primers.

The unique primer sequence is as below with underlined restriction digestion site. Forward primer contains same sequence while reverse contains the complementary sequence.

The primers are given as below:

b) Primer designing:

The primers were designed by IDT software. They are as follows,

OmpA forward primer (NcoI):

```
5',-AAAAAGACACATATG CG ATT GCAG-3',
```

OmpA reverse primer (XhoI):

```
5'-GTATCTCGAGAGCTTGCGCTGAGTTAC-3'
```

Internal primers:

```
5'-ACC AGG TTA ACC CGT ATG TTG GCT TTG-3'

5'-TGT TGA GTA CGC GAT CAC TCC TGA AAT C-3'

5'-GTT CAA CTT CAA CAA AGC AAC CCT GAA AC-3'

5'-TCG GAC AGA CCC TGG TTG TAA G-3'
```

-continued

```
5'-AGC TGG AGC CGG AGC AAC TAC TGG-3'

5'-CTG AGC TTT GTA TGC ACC GTT TTC AA-3'
```

Template DNA was prepared from *Shigella flexneri* 2a 2457t. Genes were amplified by PCR. PCR amplified product was resolved by electrophoresis and analyzed.

d) Vector preparation:

Plasmid pET28a was isolated and digested with NcoI and XhoI restriction enzyme.

Template DNA was prepared from *Shigella flexneri* 2a 2457t. Genes were amplified by PCR using the primers for 30 cycles. PCR amplified product was resolved in 1% agarose gel by electrophoresis and analyzed using Gel-Doc (Bio-Rad). PCR products were purified and digested with XhoI. Now vector plasmid pET28a was isolated and digested with NcoI and XhoI restriction enzyme.

e) Ligation:

Vector and insert was used for ligation. Insert part contains two overhang with those two restriction enzyme site. Now ligation was performed. Vector and insert was mixed with a molar ratio of 1:3 for ligation. The ligated construct was transformed into *E. coli* BL21 (DE3). The positively cloned cells were selected by using ampicilin as a selective marker. The selected cells were confirmed further by colony PCR by using the forward and reverse primers. The colonies containing the recombinant plasmid was identified and confirmed by DNA sequencing.

Recombinant protein was purified by Ni-NTA (nickel-nitrilotriacetic acid) affinity chromatography. After induction, recombinant cells were lysed by lysis buffer (composition: Benzonase, PMSF, EDTA Free Protease inhibitor cocktail, Triton X 100, Lysozyme, Benzamidine, Glycerol, Tris-HCl pH 7.5, NaCl, (3-marcaptoethanol), centrifuged at 7,000 g for 15 mins at 4° C. Now, pellet was collected and mixed with solubilization buffer (composition: Tris-HCl pH 7.5, NaCl, (3-marcaptoethanol, Urea 8 M, Imidazole). Ni-NTA resin with solubilization buffer was loaded on the column and finally the purified protein was eluted using elution buffer (Tris-HCl pH 7.5, NaCl, βmarcaptoethanol, Imidazole 500 mM) after washing with wash buffer (Tris-HCl pH 7.5, NaCl,β marcaptoethanol, Imidazole 30 Mm and 50 mM). The affinity purified fraction was dialysed in the buffer 100 mM Tris-HCl (pH-7.5)-150 mM NaCl. The expression and purity of the recombinant protein was confirmed by running on 10% SDS-PAGE.

The overexpression has been performed by the below method:

The recombinant BL21 (DE3) *E. coli* containing the OmpA gene was grown on 5 ml LB broth containing ampicillin and incubated overnight at 37° C. An aliquot of the overnight cell culture was added into another LB medium (containing 100 μg/ml ampicillin) and grown to mid log phase and incubated at 37° C. with shaking (200 rpm). Once an optical density at 600 nm of the cultures reached 0.4-0.6 (mid log), cells were induced with 0.1 mM isopropyl thiogalactoside (IPTG) in one test tube while other was not induced. Next these two were subjected to SDS-PAGE followed by western blot with anti-His antibody which confirms overexpression of OmpA protein.

The sequence of OMPA gene of *Shigella flexneri* 2a 2457T has been given below:

```
1    atgaaaaagacagctatcgcgattgcagtggcactggctggtttcgctaccgtagcgcag
61   gccgctccgaaagataacacctggtacactggtgctaaactgggctggtcccagtaccat
121  gacactggttttattcctaacaatggtccgacccacgaaaaccaactgggtgcaggtgct
181  tttggtggttaccaggttaacccgtatgttggttttgaaatgggttacgactggttaggt
241  cgtatgccgtacaaaggcgacaacatcaacggcgcatacaaagctcagggcgttcagctg
301  accgctaaactgggttacccaatcactgacgatctggacatctacactcgtctgggtggt
361  atggtatggcgtgcagacaccaaggctaacgtacctggtggcgcatcctttaaagaccac
421  gacactggcgtttctccggttttcgcaggtggtgttgagtacgcgatcactcctgaaatc
481  gctacccgtctggaataccagtggaccaacaacatcggtgacgcaaacaccatcggtact
541  cgtccggacaacggtctgctgagcctgggtgtttcctaccgtttcggtcagggcgaagca
601  gctccggtagttgctccagctccggcaccggaagtacagaccaagcacttcactctgaag
661  tctgacgttctgttcaacttcaacaaagcaaccctgaaaccggaaggtcaggctgctctg
721  gatcagctgtacagccagctgagcaacctagatccgaaagacggttccgtagttgttctg
781  ggttacactgaccgcatcggttctgacgcttacaaccagggtctgtccgagcgccgtgct
841  cagtctgttgttgattacctgatctccaaaggtatcccggcagacaagatctccgcacgt
901  ggtatgggcgaatccaacccggttactggcaacacctgtgacaacgtgaaacagcgtgct
961  gcactgatcgactgcttggctccggatcgtcgcgtagagatcgaagttaaaggtatcaaa
1021 gacgttgtaactcagccgcaggcttaa
```

Various experiments have done for the novel formulation as claimed hereafter. The detailing of the experiments and data associated with those have been discussed below:

The morphological characteristics of nano particles were examined by transmission electron microscopy. The particle size distribution will detected by Dynamic light scattering. These measurements were run at least three times with independent particle batches.

FIG. 3 depicts the intensity distribution curves for A) Chitosan, B) Chitosan with alginate C) OmpA loaded chitosan with alginate (CAOP) and D) alginates.

According to FIG. 1, FIG. 2 and FIG. 2*a*, TEM images have shown the morphological properties and surface appearance of nano particles. The chitosan nano particles have nearly spherical shape and size range of about 50-350 nm whereas size range of CAOP particles are 240-700 nm.

The respective average diameters, measured by Zetasizer, of chitosan nano particles and OmpA-loaded nano particles were approximately 240 nm and 535 nm. The PDI value of chitosan nanoparticles was 0.256 while that of OmpA-loaded chitosan nano particles was 0.199, thus indicating a narrow and favorable particle size distribution (PDI<0.5) (Table 1).

Morphological characterization, size and surface charge:

In present study the results obtained by Zetasizer revealed that the OmpA—loaded nano particles are larger than the chitosan-TPP ones, possibly due to the coating of alginate, high molecular weight and large size of the OmpA protein molecules.

The table 1 is provided which illustrates the size, PDI and zeta potential of different chitosan and alginate samples:

TABLE 1

| SAMPLE | MEAN PARTICLES SIZE (NM) | PDI | ZETA POTENTIAL |
|---|---|---|---|
| Chitosan | 136.0 nm | 0.385 | +32.70 |
| Chitosan with alginate | 249.2 nm | 0.260 | −40.54 |
| OMPA loaded chitosan with alginate | 535.9 nm | 0.470 | −20.78 |
| Alginate | 327.9 nm | 0.331 | −45.47 |

The effectiveness of the novel formulation as claimed herein after is illustrated with foregoing example:

Swiss male and female mice, six to seven weeks old, were taken from animal resource department of NICED. Mice were caged separately and maintained at 25° C. with 75% humidity and fed sterile food and water under the care of full time staff and in accordance with the rules of the institutional animal ethical committee (IAEC) (Apro/77/24/11/2O10, Reg. No. NICED/CPCSEA (AW) 215/2009-2015).

Female mice were immunized orally at days 0, 7, and 14 with 50 µg per 100 µl of purified OmpA coated with chitosan-alginate (CAOP) using the concentration. Fifteen minutes before the oral immunization; each mouse was anaesthetized by intramuscular injection of a mixture of ketamine (35 mg $kg^{-1}$ body weight; Sterfil Laboratories Pvt. Ltd, India) and xylazine (5 mg $kg^{-1}$ body weight, AstraZeneca Pharma India Ltd, India). CAOP was introduced directly into the stomach through a mouse feeding needle (Harvard Instrument, USA). The same volume of PBS was given by oral administration to the non-immunized group. All immunized and non-immunized group of mice were returned to their cages and given limited amounts of sterile food and water.

Infectious dose determination for challenge:

The infectious dose and the challenge dose of each strain were listed in table 2. The $ID_{50}$ was considered to be the dose which ensured ~$10^6$-$10^7$ bacteria per gram of intestine of the challenged neonates, after six hour incubation in 3 to 4 days old suckling mice.

TABLE 2

$ID_{50}$ and challenge dose of *Shigella* strains

| STRAIN | INFECTIOUS DOSE$_{50}$ ($ID_{50}$) ($\times 10^8$ $ML^1$) | CHALLENGE DOSE ($\times 10^9$ $ML^1$) |
|---|---|---|
| *S. dysenteriae* 1 (NT4907) | 1 ± 0.241 | 5 ± 0.356 |
| *S. flexneri* 2a (2457T) | 3 ± 0.151 | 4 ± 0.158 |
| *S. sonnei* (IDHO0968) | 1 ± 0.275 | 5 ± 0.141 |

Values are means ± SEM of three independent experiments.

We used female mice model to measure the protective efficacy and to study the immune responses that are elicited following disease or immunization. Two groups of mice (Immunized and Control, weighing between 25 g) were selected for oral immunization with *Shigella* protein OmpA coated with chitosan-alginate. Each group contained 10 mice. The immunization experiment was done according to the method of Sack et al (1988) and the challenge experiment was done according to the method of Fernandez et al. (2003).

100% homologous protection was observed against virulent wild serotype while in average 75% was achieved in heterologous protection challenged by *S. dysenteriael* (NT4907) and *S. sonnei* (IDH00968). High reciprocal increase of serum lgG antibody titer was observed during the period of immunization.

Immunoblot data of whole cell lysate (WCL) also supported strong homologous protection as well as heterologous protection against CAOP immunization.

TABLE 3

First and second challenge study in suckling mice from immunized mother

| CHALLENGED STRAIN | EXPERIMENTAL GROUP | NO. OF NEONATES IN EACH GROUP | % O OF SURVIVAL AFTER FIRST CHALLENGE | PROTECTIVE EFFICACY L % L AFTER FIRST CHALLENGE | % OF SURVIVAL AFTER SECOND CHALLENGE | PROTECTIVE EFFICACY A (% L AFTER SECOND CHALLENGE |
|---|---|---|---|---|---|---|
| *S. dysenteriae* | Control | 10 | 10 (1/10) | 77.78 | 20 (2/10) | 77.78 |
| 1 (NT4907) | Immunized | 10 | 80 (8/10) | | 90 (9/10) | |
| *S. flexneri* | Control | 10 | 10 (1/10) | 100 | 10 (1/10) | 100 |
| 2a (2457T) | Immunized | 20 | 100 (20/20) | | 100 (10/10) | |
| *S. sonnei* | Control | 10 | 10 (1/10) | 88.89 | 20 (2/10) | 77.78 |
| (IDH00968) | Immunized | 10 | 90 (9/10) | | 90 (9/10) | |

[a]Protective efficacy was calculated as {[(percent deaths of non-immunized mice) − (percent deaths of immunized mice)] ÷ [percent deaths of non-immunized mice]} × 100.

Death or visible side effects due to toxicity (such as ruffled fur or lethargy or diarrhea or weight loss) did not occur in mice after three successive oral immunizations with 50 µg of purified OmpA coated with chitosan-alginate (CAOP). A significant level of protection after both first and second challenge studies were achieved in newborn mice of immunized dams. Most of the suckling mice from non-immunized mother became sick and eventually died between 10 and 16 hr of incubation (Table 4). More or less same results were obtained after both challenge studies. Control mice from non-immunized groups showed higher intestinal colonization (~$10^7$ CFU/gm of intestine) leading to Shigellosis. Dead mice from immunized groups showed colonization ~$10^5$ CFU/gm of intestine which was 100 fold lower than the rate of intestinal colonization in control mice (~$10^7$ CFU/gm of intestine) and alive neonates showed even lesser intestinal colonization (~$10^3$ CFU/gm of intestine). CAOP conferred 100% protection against *S. flexneri* 2a after both challenge studies. Protective efficacies against *S. dysenteriae* 1 and *S. sonnei*, (Table 3) were above 75%. The above results suggest CAOP immunization could confer 83-100% passive protection against shigellosis in neonatal mice model.

Protective Efficacy Against Shigellosis to the Neonatal Mice:

The aim of our study is to develop an oral subunit vaccine with *Shigella* protein OmpA coated with chitosan-alginate.

M. ELISA:

Blood was collected at days 0, 7, 14, 28, 35, 56, 72 and 120, after the first oral immunization. The collected blood was allowed to clot at room temperature (RT) for 30 min and serum was isolated by removing the blood clot with a sterile toothpick, followed by centrifugation (91 g, 10 min and 4° C.). After adding sodium azide (final concentration 0.05%), the sera were stored at −80° C. (Schild et al., 2008) until use. IgG (whole molecule) response in immunized and non-immunized sera were measured by ELISA, essentially following the method developed by Keren (1979). Disposable polystyrene (Nunc, Denmark) microtiter wells were coated with 100 µL of CAOP and incubated for 18 h at 4° C. Wells were washed three times with PBS (pH 7.4). Nonspecific binding sites were blocked by incubating the wells with 200 uL of 5% bovine serum albumin (BSA; Sigma Chemical) for 2 h at 37° C. The wells were washed three times with PBS-T (PBS with 0.5% Tween-20) and incubated with serially diluted serum samples at 37° C. for 1" h. Following washing, 100 µL HRP-conjugated goat anti-mouse immunoglobulin (Sigma Chemical) was added to each well and the plate was incubated at 37° C. After washing with PBS, the substrate o-phenyl-D-amine (OPD) was added to each well. The reaction was stopped after 10 min by adding 100 µL of 2 N Sulphuric acids and the reading was taken at 492±2 nm wave length using an ELISA reader. The experiments were repeated three times with the immunized and non-immunized serum, collected from individual mice, before, during and after the immunization period.

FIG. 4 illustrates these test results clearly with the help of a graph.

Western Blot Analysis

Whole cell lysates (WCL) of six virulent strain of *Shigella* sp, *S. dysenteriae* 1Δstx NT4907, *S. boydii* type 4 BCH612, *S. sonnei* IDH00968, *S. flexneri* 2a 2457T, *S. flexneri* 3a C519, *S. flexneri* 6 C347 were resolved by SDS-PAGE followed by immunoblot using alkaline phosphatase conjugated lgG (whole-molecule), according to the protocol described previously.

Immunoblot by anti-CAOP sera against WCL (FIG. 9) demonstrated that CAOP antiserum cross reacted with the whole cell lysates of *S. dysenteriae* 1Δstx NT4907, *S. boydii* type 4 BCH612, *S. sonnei* IDH00968, *S. flexneri* 2a 2457T. *S. flexneri* 3a C519, *S. flexneri* 6 C347. The recombinant protein also showed reactivity with mouse antisera produced by challenged with whole cell virulent *S. flexneri* 2a suggesting the strong immunogenicity of the recombinant OmpA. This also proved that the antigenicity of the protein is maintained. As chromosomally encoded OmpA protein is conserved among *Shigella* strains and *E. coli* strains it will give heterologous protection against not only *Shigella* species but also against pathogenic *E. coli* strains.

The novel formulation helps to protect the protein from acid barrier of stomach and chitosan being mucoadhesive can adhere with the mucus membrane and increase the bioavailability of the protein.

Hence, this innovative formulation provides substantially higher immunogenicity and protective efficacy than that of OmpA protein itself.

We claim:

1. An oral formulation of outer membrane protein A (OmpA) comprising essentially of:

a) OmpA protein as an active molecule, obtained as a product of an OmpA gene derived from *Shigella flexneri* 2a 2457T, inserted in a plasmid comprising a set of a forward and a reverse primer set; and b) Alginate chitosan nanoparticles as a vehicle;

wherein the formulation has a particle diameter in a range of 240 nm to 700 nm;

wherein the formula is administered orally;

wherein the formulation has a mean particle size of 535.0 nm, a particle size distribution of 0.470 and a zeta potential of −20.78;

wherein the forward primer has a nucleotide sequence 5'-AAAAAGACACATATG CG ATT GCAG-3' (SEQ ID NO: 1) and the reverse primer has a nucleotide sequence 5'-GTATCTCGAGAGCTTGCGCTGAGTTAC-3' (SEQ ID NO: 2); and, wherein bases "CATATG" in the forward primer represents restriction site specific for NcoI and the bases "CTCGAG" in the reverse primer represents restriction site specific for XhoI.

2. A method of preparation of an oral formulation of an outer membrane protein A (OmpA), the method comprising the steps:

a) preparing a recombinant plasmid comprising an OmpA forward primer having a nucleotide sequence 5'-AAAAAGACACATATG CG ATT GCAG-3' (SEQ ID NO: 1) and an OmpA reverse primer having a nucleotide sequence 5'-GTATCTCGAGAGCTTGCGCTGAGTTAC-3' (SEQ ID NO: 2)

wherein the bases "CATATG" in the forward primer represents restriction site specific for NcoI and the bases "CTCGAG" in the reverse primer represents restriction site specific for XhoI;

b) transferring the recombinant plasmid to *E. coli* BL21 (DE3) for multiplication;

c) isolating OmpA protein as a product from the *E. coli* BL21 (DE3);

d) preparing chitosan with alginate nanoparticles; and e) loading OmpA protein into said chitosan with alginate nanoparticles;

wherein the formulation has a particle diameter in a range of 240 nm to 700 nm;

wherein the OmpA is derived from *Shigella flexneri* 2a 2457T;

wherein the formulation is configured for an oral administration; and wherein the formulation has a mena particle size of 535.9 nm, a particle size distribution of 0.470 and a zeta potential of −20.78.

3. The method as claimed in claim 2, wherein preparing the plasmid is performed by common restriction sites specific to restriction enzymes NcoI and XhoI.

4. The method as claimed in claim 2, wherein preparing the plasmid is performed through ligation of the plasmid and said primers by mixing the plasmid and primers in a molar ratio of 1:3.

5. The method as claimed in claim 2, wherein isolating OmpA protein as a product from the *E. coli* BL21 (DE3) is performed in the mid log phase of said bacteria.

6. The method as claimed in claim 2, wherein preparing chitosan nanoparticles comprises the steps of:

a) preparing a chitosan solution by dissolving chitosan in 1% (v/v) acetic acid solution at a concentration of 2 mg/ml;

b) preparing an anionic tripolyphosphate (TPP) solution by dissolving TPP in distilled water at a concentration of 1 mg/ml;

c) adding the TPP solution into the chitosan solution dropwise at 1:2 ratio;

d) forming chitosan colloid nanoparticles under mild agitation in room temperature condition;

e) formulating colloid chitosan nanoparticles at room temperature during centrifugation at 35,000 rpm for 1 hr.;

f) discarding supernatant and re-dispersing deposit in distilled water to obtain chitosan nanoparticles.

7. The method as claimed in claim 2, wherein loading the OmpA protein into said chitosan with alginate nanoparticles comprises the steps of:

a) redispersing a colloid of said chitosan nanoparticles in 25 ml of distilled water at a concentration of 2 mg/mL under continuous ultrasonication to disaggregate the nanoparticles;

b) loading OmpA protein subunit into the chitosan nanoparticles by incubating OmpA protein obtained as a product from the *E. coli* BL21 (DE3) with said nanoparticles under mild agitation for 15 minutes at room temperature condition to make final concentration of OmpA protein 1 mg/mL;

c) adding dropwise OmpA-loaded chitosan nanoparticles suspensions with pH 5.1 into sodium alginate solution at a concentration of 1 mg/mL under mild agitation at pH 7 for 10-20 minutes;

d) centrifuging the resulting suspension at 3400 rpm for 5 minutes and discarding the supernatant to obtain alginate coated chitosan nanoparticles; and e) redispersing alginate coated chitosan nanoparticles into an aqueous solution of calcium chloride ($CaCl_2$) at a concentration of 0.524 mmol/L to crosslink the alginate layer present on the surface of chitosan nanoparticles.

* * * * *

UNITED STATES PATENT AND TRADEMARK OFFICE
CERTIFICATE OF CORRECTION

| | |
|---|---|
| PATENT NO. | : 11,298,415 B2 |
| APPLICATION NO. | : 16/093237 |
| DATED | : April 12, 2022 |
| INVENTOR(S) | : Hemanta Koley et al. |

It is certified that error appears in the above-identified patent and that said Letters Patent is hereby corrected as shown below:

In the Claims

Column 15, Line 59, Claim 2, delete "mena" and insert -- mean --

Signed and Sealed this
Twenty-third Day of August, 2022

Katherine Kelly Vidal
*Director of the United States Patent and Trademark Office*